United States Patent [19]
Proctor et al.

[11] Patent Number: 5,197,468
[45] Date of Patent: Mar. 30, 1993

[54] DEVICE FOR PROTECTING AN ELECTRONIC PROSTHESIS FROM ADVERSE EFFECTS OF RF AND/OR ELECTROSTATIC ENERGY

[76] Inventors: Paul W. Proctor, Rte. 2, Kathy La., White Plains, Md. 20695; Robert L. Dow, Rte. 5, Box 415, LaPlata, Md. 20646

[21] Appl. No.: 888,870

[22] Filed: May 27, 1992

Related U.S. Application Data

[63] Continuation-in-part of Ser. No. 866,512, Apr. 10, 1992, and Ser. No. 794,126, Nov. 12, 1991, abandoned, which is a continuation-in-part of Ser. No. 584,045, Sep. 18, 1990, which is a continuation-in-part of Ser. No. 479,117, Nov. 12, 1991, Pat. No. 5,036,768, said Ser. No. 866,512, is a continuation-in-part of Ser. No. 584,045, Nov. 12, 1991.

[51] Int. Cl.$^5$ .............................................. A61N 1/36
[52] U.S. Cl. ........................... 128/419 PG; 128/734; 128/419 PT
[58] Field of Search .......... 128/419 PG, 734, 419 PT, 128/419 P, 784, 785, 901

[56] References Cited

U.S. PATENT DOCUMENTS

| | | | |
|---|---|---|---|
| 4,870,341 | 9/1989 | Pihl et al. | 128/734 |
| 5,003,975 | 4/1991 | Hafelfinger et al. | 128/419 PT |
| 5,095,902 | 3/1992 | Ljungstroem | 128/419 PG |

*Primary Examiner*—William E. Kamm
*Assistant Examiner*—George Manuel
*Attorney, Agent, or Firm*—Terry M. Gernstein

[57] ABSTRACT

An implantable prosthesis, such as an artificial cardiac pacer, or the like, is protected from misoperation caused by RF energy and/or electrostatic energy incident thereon by a protective device attached to the lead wire connecting the device to tissue stimulating electrodes or other such electrodes mounted in a patient. The protective device is the device disclosed in U.S. patent application Ser. Nos. 07/794,125, 07/584,045 and 07/866,512. The protective device includes a Ferrite body electrically and thermally connected to the lead wire and to a ground element, such as the housing for the prosthetic device. The Ferrite body, in conjunction with the lead and the ground element, has an impedance that exceeds the impedance established between the lead wire and ground when the device is exposed to RF energy.

21 Claims, 4 Drawing Sheets

DEVICE FOR PROTECTING AN ELECTRONIC PROSTHESIS FROM ADVERSE EFFECTS OF RF AND/OR ELECTROSTATIC ENERGY

This application is a continuation-in-part of U.S. Ser. No. 07/866,512 filed on Apr. 10, 1992, which was a continuation-in-part of 07/584,045 filed on 04/10/92, which was a continuation-in-part of U.S. Ser. No. 07/479,117 now U.S. Pat. No. 5,036,768; and 07/794,126, filed on 11/12/91 now abandoned, which was a continuation-in-part of 07/584,045. The disclosures of these documents are incorporated herein by reference.

TECHNICAL FIELD OF THE INVENTION

The present invention are to the general art of medical protheses, and to the particular field of electronic prostheses that are implanted into a user's body.

BACKGROUND OF THE INVENTION

A wide variety of medical prostheses are implanted into hundreds of thousands of people worldwide each year. These devices perform many roles, from relieving pain, restoring functions lost due to injury or disease, to ultimately extending life, and improving the quality of life.

Hundreds of thousands of people are alive today because their deficient heart is aided by an artificial cardiac pacer, while many thousands who would be crippled and in constant pain from arthritis can walk with ease due to various other prostheses. Implants have been developed, and are being developed, to prevent fatal arrhythmias, to replace the entire human heart, to help some deaf persons to hear, to help the paralyzed move their muscles, to pump drugs where they are most needed, to stimulate the growth of bone, to help heal difficult fractures, and many more functions.

Most of these implants were practically unknown before 1950. With the exception of dental implants, few implants were used before 1960. New developments in materials science, along with developments in electronics have made these devices possible and within the reach of nearly everyone. For example, implanted prostheses have been used in the following situations:

| Device | Application |
|---|---|
| Automatic implantable defibrillator | Defibrillate arrhythmic heart |
| Bladder stimulator | Restore lost bladder control |
| Bone growth stimulator | Heal difficult fractures |
| Artificial Cardiac pacer | Correct arrhythmia in heart |
| Cerebellar stimulator | Control spasticity in epilepsy; Control seizures in epilepsy; Control severe psychosis; |
| Deep brain stimulator | Control pain |
| Diaphragm pacer | Restore lost breathing control |
| Peripheral nerve stimulator | Control pain |
| Peroneal nerve stimulator | Improve gait in hemiplegics |
| Scoliosis stimulator | Improve scoliotic curve |
| Spinal cord stimulator | Control pain Control spasticity Control systems of multiple sclerosis |

The basic rationale for the implantation of an electronic device is the performance of some function within the body without the need for bringing wires through the skin. The majority of electronic implants work by delivering an electrical stimulus to excitable tissue such as nerve or muscle.

While the inventors contemplate that the best mode of their device is used in an artificial cardiac pacer, it is to be understood that the invention disclosed herein will be equally applicable to the other devices listed above.

The artifical cardiac pacer is the most successful and best known of the implantable electronic devices. Hundreds of thousands of pacers, manufactured by over two dozen companies, are implanted annually. There are so many companies that produce such equipment that there is actually a directory "Guide to Cardiac Pacemakers," published by Droege Computing Services, Inc of Durham, NC listing all of the artifical cardiac pacers and associated products.

The generation of natural pacing stimulus, the conduction of that stimulus, and the contraction of cardiac muscle in response to the stimulus are all events that are marked by an electrical depolarization of the muscle or nerve cell membranes. Electronic artificial pacers are primarily used to treat defects in the natural pacer or it conduction system. Electronic stimuli are substituted for irregular or absent natural stimuli. One such defect, for which pacers saw some of their earliest use, is atrio-ventricular block, or Stokes-Adams syndrome. In this case, the electronic pacer delivers a substitute stimulus to an electrode located at the ventricle. Other heart rhythm defects have also been treated with heart pacing.

Pacing electrodes or leads can be surgically attached to the surface of the heart or more conveniently can be placed through a large vein into the heart chamber that is to be paced. Bipolar configurations are used where both output or sensing electrodes are placed within the heart chamber, as are unipolar configurations where one electrode, the cathode, is in the chamber and the anode is the pacer housing itself. Bipolar electrodes are less sensitive to interference when used as sensing electrodes in demand cardiac pacer applications.

Early artificial cardiac pacers were simple fixed-rate oscillators that were coupled to a single ventricular electrode. In later pacers, a form of feedback control is utilized to adapt pacer function to more subtle rhythm defects. Sensing amplifiers are used to detect the presence or absence of natural cardiac events by measuring the ECG correlate of those events from intracardiac electrodes. In a simple demand pacer, for example, the pacer would not stimulate unless it sensed an absent ventricular signal, a certain time interval after the occurrence of the last QRS. Therefore, if the natural rhythm is slower than the preset pacer rhythm, the pacer rhythm prevails; if the natural rhythm is faster, the natural rhythm prevails. Other complex pacers sense atrial activity and stimulate the ventricles in synchrony with atrial contraction. Still other "physiolic" pacers stimulate both the atrium and the ventricle while sensing activity in these two chambers and utilizing logic to determine the appropriate stimulus based on the sensed information. As technology has progressed, the artifical cardiac pacer has evolved such that their programmability has become even more sophisticated. In striving to improve the quality of life of some patients, the industry has developed many sophisticated heart pacers that attempt to mimic the heart's natural responses to body needs as closely as possible. The number of different artificial cardiac pacers has increased so greatly that the Intersociety Commission for Heart Disease Resources has published a code for standard pacemaker terminology to describe different pacer function types.

However, with this increasing sophistication has come a concomitant increase in sensitivity of the artificial cardiac pacers to misoperation due to external influences. For example, such external influences as RF energy, electrostatic energy, vibration and the like have been identified as causing problems with artificial cardiac pacers. The literature is replete with examples of cardiac pacer misfunctions traced to helicopter aeromedical transport, medical procedures such as radiofrequency catheter ablation, MRI techniques, electrocautery techniques, dental procedures as well as several other medical procedures. The hazards of exposure to RF or electrostatic energy in non-medical situations have also been identified and reported in the medical journal articles. It has also been determined that the strength of the RF field is as important as the proximity of the RF field source to the artificial cardiac pacer, or more importantly its leads.

The effects of such external influences on an artificial cardiac pacer have been identified as falling into two main categories: temporary and permanent.

There are two main temporary effects. Such interference may be detected and identified as noise to cause the artificial cardiac pacer to revert it its "interference" mode and give a constant predetermined output rate; and such interference may cause the pacer to falsely identify the interference as being of cardiac origin and give rise to "missing" pulses or to an erroneous output rate.

Permanent effects caused by such interference may result in the pacer output being totally inhibited or shut down. In extreme cases, the wearer may be injured.

Therefore, the art has included several means for overcoming these problems. For example, modern pacers are often hermetically sealed in a metal case which effectively screens the internal circuitry against normally encountered levels of electromagnetic radiation in the manner of a Faraday shield. However, these housings are not perfect Faraday shields, and some radiation may leak through openings in the shield or affect the circuitry via the leads that connect the main control circuitry to the electrodes spaced about the user's body. Some pacers have looped wires in an attempt to cancel stray RF signals. Others include special interference circuitry included therewith. Still other pacers include special RF filters and the like.

While some of the adverse effects associated with external RF or electrostatic energy can be alleviated by these techniques, modern pacers are often exposed to ever-increasing amounts of such energy. Therefore, any deficiencies in such protection means may be exacerbated by such exposures. Therefore, even more effective techniques and means for protecting modern artificial cardiac pacers from the adverse effects of both RF energy and electrostatic energy must be found.

However, with the ever-increasing sophistication of modern pacers, the protection means must not be expensive or complex in order to keep costs and complications to a minimum. Therefore, while such new means and techniques are necessary, they cannot add undue amounts of expense or complications to the artificial cardiac pacer.

In the prior patent applications referenced above, the present inventors disclose a device for protecting electronic equipment from both the effects of RF energy from broadcast through radar frequencies and electrostatic energy. As discussed in these patent applications, the device disclosed therein can protect electronic equipment from directly coupled, impedance matched RF energy as high as nineteen watts at one MHz. Many sources that expose artificial cardiac pacers to RF energy generate such RF energy in this frequency range, and at coupled energy levels far less than the nineteen watts. Still further, these devices have been tested and will protect associated electronic equipment from electrostatic energy levels as high as 12.5 Joules. Many prosthesis devices should never experience these levels of electrostatic energy.

Accordingly, the device disclosed in the incorporated patent applications is ideal for protecting implanted electronic prosthetic devices from adverse effects of both RF and electrostatic energy.

Still further, since many of these implanted electronic devices are encased in metal housings, such housings can be modified to become complete Faraday shields by incorporating the inventors' ferrite devices. The use of the protective device disclosed in the aforementioned patent applications in the formation of a Faraday shield is discussed in U.S. Pat. Application Ser. No. 07/794,126, the disclosure of which is incorporated herein by reference.

Accordingly, there is a need for a device that can effectively protect an implanted electronic device against undesired operation caused by exposure to RF and/or electrostatic energy. In particular, there is a need for a device that will protect an artificial cardiac pacer against undesired operation caused by exposure of the artificial cardiac pacer to RF and/or electrostatic energy.

OBJECTS OF THE INVENTION

It is a main object of the present invention to provide a protective device that can effectively protect an implanted electronic device against undesired operation caused by exposure to RF and/or electrostatic energy.

It is another object of the present invention to provide a protective device that can effectively protect an artificial cardiac pacer against undesired operation caused by exposure to RF and/or electrostatic energy.

It is another object of the present invention to provide a protective device that can effectively protect an implanted electronic device against undesired operation caused by exposure to RF and/or electrostatic energy in a simple, inexpensive manner.

It is another object of the present invention to prevent stray RF signals from reaching the circuitry of medical prosthesis devices and being interpreted or utilized incorrectly.

It is another object of the present invention to minimize burnout of electrical components inside electrical prosthesis devices due to RF energy overpowering the electrical components.

It is another object of the present invention to prevent disruptive levels of electrostatic energy from reaching medical prosthesis circuitry.

It is another object of the present invention to prevent damaging levels of electrostatic energy from reaching the circuitry of medical prosthesis devices.

It is another object of the present invention to prevent inadvertent speed up of artificial cardiac pacers due to exposure to electrostatic energy.

It is another object of the present invention to protect medical prosthesis circuits from stray RF energies having frequencies in the range of near 1 MHz to above 22 gigahertz without detectable resonant frequencies.

It is another object of the present invention to prevent detectable levels of RF energy above 0.5 MHz from reaching medical prosthesis circuitry.

It is another object of the present invention to provide a single protective device that protects medical prosthesis circuits from both stray RF and electrostatic energy sources.

It is another object of the present invention to provide a single protective device that provides a combination RF and electrostatic protection regardless of the number of leads or sensors used by a medical prosthesis device.

It is another object of the present invention to protect medical prosthesis circuitry from both RF and electrostatic energies from entering the circuitry either through the leads or through one lead and the metal case on the outside of the medical prosthesis device.

It is another object of the present invention to provide a complete faraday shield around medical prosthesis devices.

It is another object of the present invention to expand the number of medical diagnostic tools available to users of medical prosthesis devices.

It is another object of the present invention to simplify procedures and techniques required of surgeons using electrosurgical devices operating on patients having a medical prosthesis.

It is another object of the present invention to transfer all of the technologies and techniques previously discovered by the inventors and disclosed in the incorporated documents to the protection of medical prostheses.

SUMMARY OF THE INVENTION

These, and other, objects are achieved by incorporating the protective device disclosed in the incorporated patent applications and the incorporated patent into an implanted electronic device, such as an artificial cardiac pacer. The protective device includes a Ferrite body that is electrically and thermally connected to a lead wire and to ground, such as the housing of the electronic equipment. As discussed in the incorporated documents, the protective device bleeds electrostatic energy and shunts RF energy to ground before such energy reaches the electronic equipment connected to the lead or leads, on either end of the lead or leads. The internal dc resistance of the Ferrite body is higher than the dc resistance of the electronic equipment so shorting does not occur, yet the impedance of the Ferrite body in conjunction with the ground is higher than the impedance existing between the lead and ground when RF energy is incident on the device. In this manner, potential induced by RF energy incident on the device "sees" an impedance to ground that is less than the impedance to the electronic equipment, and any induced current flows preferentially to ground rather than entering the electronic equipment.

The non-destructive bleeding of electrostatic energy occurs in a manner that permits the device to be exposed to repeated doses of electrostatic energy without damage to the device. In fact, tests have indicated that the internal resistance and capacitance values of the device do not change even though the device has been repeatedly exposed to high levels of electrostatic energy. Such a feature produces a high degree of reliability for devices such as artificial cardiac pacers.

BRIEF DESCRIPTION OF THE DRAWINGS FIGURES

DETAILED DESCRIPTION OF THE PREFERRED EMBODIMENT OF THE INVENTION

Figure 1:
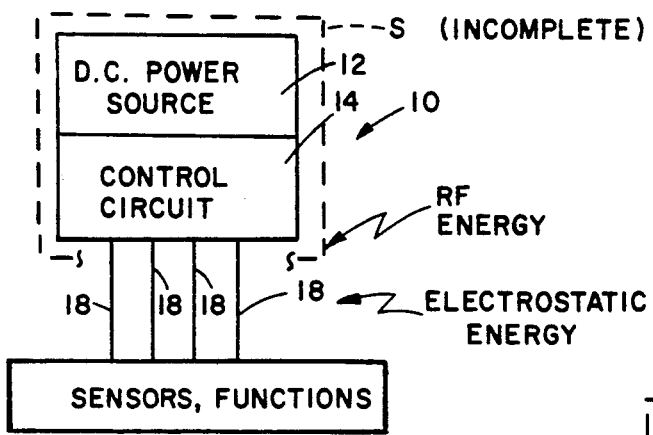
FIG. 1 is a schematic showing a prior art implantable electronic prothesis device in which RF or electrostatic energy incident on the device may cause undesired operation of the device.

A general set up for an implantable electronic device 10 is indicated in FIG. 1. The device includes a dc power source 12 electrically connected to a control circuit 14 and to sensors, simulators or the like, generally indicated in box 16 via leads 18. While several leads are shown, it is understood that as few as two leads and as many as desired can be used depending on the functions associated with the device. The sensors and other elements indicated in box 16 are located throughout the patient's body. These sensors can serve to stimulate tissue, sense conditions of the patient for use in setting functions in the control circuit 14, or the like. There is an imperfect faraday shield surrounding the implantable device that allows RF leakage and electrostatic energy to enter the circuit.

As discussed above, the device 10 maybe exposed to RF energy or electrostatic energy from many sources. It has been determined that such energy may create a potential across the leads 18 that can cause damage to the device or cause undesired operation of that device.

The present invention prevents such RF-induced and/or electrostatic-induced potential from every reaching the elements of the device located on either end of the lead wires 18 by either absorbing the energy or by dissipating it to ground. The device is fully disclosed in the incorporated documents, and thus the full details thereof will not be presented here, reference being made to such documents for details.

Figure 2:
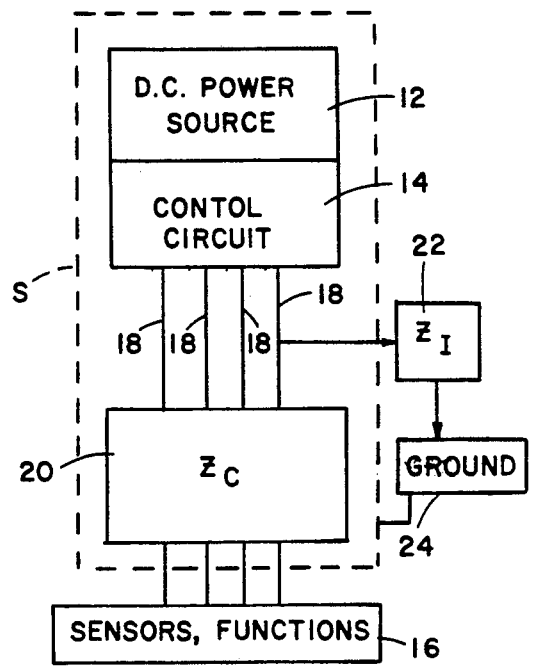
FIG. 2 is a schematic showing how the prior art implantable electronic prothesis is modified according to the present invention to include an impedance between a dc power source and the electronic elements located in the patient that exceeds the impedance between lead wires and ground.
Figure 2A:
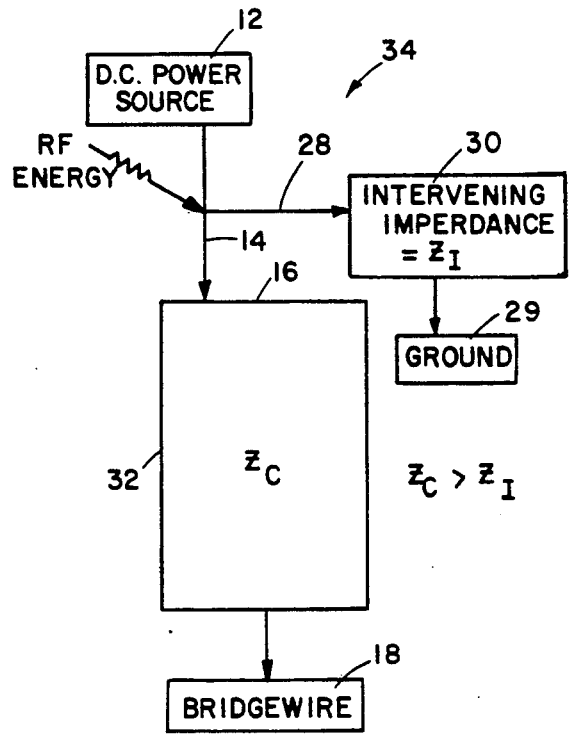
FIG. 2A is a block diagram representing the invention disclosed in the incorporated documents in which the electrical path through an input lead to a bridgewire in an EED has an impedance that is higher than an alternative electrical path to ground.
Figure 2B:
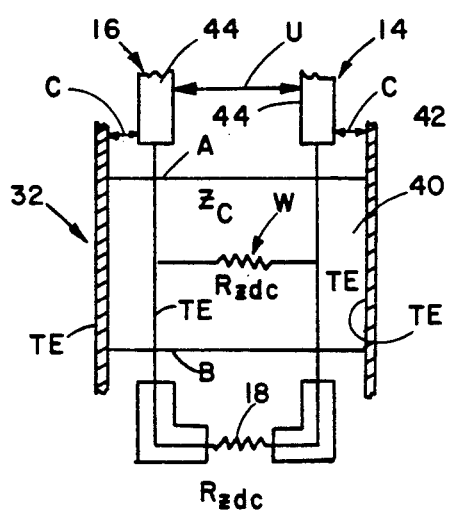
FIG. 2B is a block diagram representing one embodiment of the invention shown in the incorporated documents in which an EED includes a Ferrite element electrically and thermally connected to the input leads of the EED and to the electrically and thermally conductive case of the EED.

For reference, the invention disclosed in the incorporated documents will be reviewed with regard to FIGS. 2A and 2B. As shown in FIGS. 2A and 2B, the invention disclosed in the incorporated documents is embodied in a means for increasing the value of the impedance on input leads 14x and 16x between the dc power source 12x and the bridgewire 18x to a value greater than that impedance $Z_I$ associated with the path 28x from the input leads to each other or from the input leads to the ground element 29x. In this manner, the energy associated with the RF energy incident on the EED will either be simply blocked by the impedance on the input leads, or will move to ground via the lower impedance path 28x to ground instead of moving through the input leads to the bridgewire.

This is illustrated in FIG. 2A by impedance element 32x located in the input leads 14x and 16x between the dc power source 12x and the bridgewire 18x of EED 34x. The impedance element 32x has an impedance $Z_C$ which is greater than the impedance value $Z_I$ whereby the energy associated with RF energy incident on the EED 34x will "see" a path of lower impedance to ground than to the bridgewire 18x. This energy will therefore tend to flow to ground instead of to the bridgewire.

Once the RF energy or frequency exceeds the critical values discussed in the incorporated documents, the EED 34x forces the energy to ground instead of permitting it to pass to the bridgewire.

Since the value of $Z_I$ is determined according to the material properties of the path 28x, this value can be obtained from various handbooks, such as the "Handbook of Modern Electronics and Electrical Engineering" edited by Charles Belove and published in 1986 by Wiley Interscience, see e.g., Chapters 8 and 9 of this handbook, the disclosure of which is incorporated herein by reference. The value of $Z_C$ is also determined according to the properties of the materials, and can be determined by using the same standard handbooks, as well as special textbooks, such as "Ferrities" by J. Smit and H. P. J. Wign and published in 1959 by John Wiley & Sons. See e.g., pages 229 to 297, the disclosure of which is incorporated herein by reference. Other handbooks, such as Mechanical Engineers' Handbooks or Electrical Engineers' Handbooks, Physics Handbooks and the like all contain information necessary to determine the values of $Z_I$ and $Z_C$.

A preferred form of the impedance element 32x is shown in FIG. 2B as including a Ferrite element 40x electrically connected to the input leads 14x and 16x and electrically connected to electrically conductive case 42x of the EED. The electrical connection between the input leads and the Ferrite element is effected by skinning insulation 44x form the leads 14x and 16x and establishing direct electrical connection between the leads and the Ferrite element inside that element as shown in FIG. 2B. However other electrically conductive paths through the Ferrite element and can be used, such as special elements of the like. The only requirement is that the input lead electrical path make electrical contact with the Ferrite element. Preferably, this electrical contact between the input lead and the Ferrite element occurs over substantially the entire length of the Ferrite element as measured along the input leads between locations Ax and Bx shown in FIG. 2A. By being electrically connected to the Ferrite element over substantially the entire length of the input lead, any variations in physical properties of the Ferrite element are "averaged out" so the overall properties of the impedance element are predictable. Likewise, the Ferrite element 40x is electrically connected to the case 42x over substantially the entire length of the Ferrite element as measured along the case between points Ax and Bx. This electrical connection between the Ferrite element and the conductive case over substantially the entire length of the Ferrite element also "averages out" any variations in Ferrite properties as may occur. Such electrical connection increases the impedance existing in the input leads between the dc power source and the bridgewire 18x by adding the impedance of the Ferrite element 40x and the impedance associated with the case 42x to the wires in a direct electrical connection rather than via an indirect manner which would occur if the Ferrite element were electrically insulated from the input leads and from the case 42x. Therefore, the value of $Z_C$ corresponds to the total impedance of the firing input leads plus the impedance associated with the conductive case plus the impedance associated with the Ferrite element 40x; whereas the value of $Z_I$ corresponds to the impedance of the path between the firing input leads (pin-to-pin) at location Ux, or to the impedance between either input lead and the conductive case at locations Cx (pin-to-case).

However, while increasing the impedance on the input leads of the EED 34x, the direct electrical connection between the electrically conductive Ferrite element 40x and both of the input leads 14x and 16x creates an electrical path between the lead 14x and the lead 16x and between both of these leads and the electrically conductive case 42x. This path can short the leads and prevent a dc current from the dc power source from activating the bridgewire in a case where firing of the EED is intended.

To prevent this shorting of the leads 14x and 14x, the Ferrite element 40x is selected to have an internal resistance 44x that is in excess of the resistance associated with the bridgewire. As indicated in FIG. 2A, the internal dc resistance $R_{Zdc}$ associated with the Ferrite element which tends to define a dc electrical path between the input leads 14x and 16x, is grater than the dc electrical resistance $R_{Bdc}$ associated with the bridge wire 18x. In this manner, the dc path between the input leads and each other and between the input leads and the conductive case has a dc resistance great enough so that the dc firing current will flow to the bridgewire rather than be shorted from one input lead to the other or from one input lead to the case.

Specifically, it has been found that Ferrite elements having an internal dc resistance of between 3,000 ohms and 50,000 ohms have had sufficient dc resistance to prevent a dc firing signal from being shorted away from the bridgewire. Most specifically, a dc internal resistance $R_{Zdc}$ of approximately 3,800 ohms has been determined as being optimal.

While various forms of Ferrite can be used, the preferred form of the Ferrite element 40x is sold by Ceramic Magnetics Corp. of Fairfield, NJ under the name MN-67. Another effective material for the Ferrite element 40x is sold by the same company and has an elemental analysis that corresponds to $MnO_{0.45}Zn_{0.3}FeO_{0.25}Fe_2O_4$. This particular formulation provides a significant RF attenuation below one megahertz and is even effective above the 20 gigahertz region. In fact, this formulation provides significant RF attenuation even in the 10 kilohertz region. Furthermore, the Curie Temperature of this material is in the range of about 250° C. to about 280° C. This high Curie Temperature has not been available before in combination with the other desirable physical properties stated above. Heretofore, the maximum heating that the inventors have been able to obtain using prior EEDs is about 90° C. The Ferrite element formed of this material can be processed to give strong Ferrite devices that withstand assembly operations without excessive breakage.

This formulation can be produced into several different Ferrite devices, including one hole beads, two hole baluns, or multiple hole chokes. It has been observed that the RF power attenuated by these devices increases in the order listed. For purposes of this disclosure, a bead has one hole, and is placed on a lead in the manner of a strung bead; a balun has two holes and can accommodate two wires or conductors; and a choke has multiple holes.

It has also been found that the direct electrical contact between the Ferrite element 40 and the case and the input leads tends to dissipate static electricity by providing a direct electrostatic path to ground. Due to this direct electrostatic path to ground, the EED 34 can withstand electrostatic potentials which are extremely high as compared to those electrostatic potentials which will cause the bridgewire of EED 10' to fire while not requiring any additional elements to dissipate static discharge.

It is noted here that the protective device 20, shown in FIG. 2, is electrically and thermally connected to the leads 18 so that the impedance on the leads, $Z_C$, exceeds the impedance 22, indicated in FIG. 2 as $Z_I$, between the leads 18 and ground 24. This situation is indicated in FIG. 2 as $Z_C > Z_I$. As will be discussed below, the present invention also contemplates encasing the elements 12, 14, 20, 22 and 24 as well as the leads connecting those elements together in a complete faraday shield F.

Figure 3:
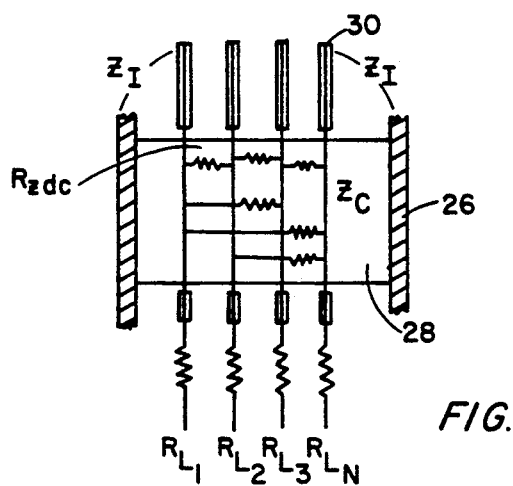
FIG. 3 is a schematic showing the electrical and thermal connection between the leads and the protection device and the housing of an implantable electronic prosthesis according to the present invention.

The electronic schematic is indicated in FIG. 3, with the ground being the housing 26, and $Z_C$ being a body of Ferrite material 28. As is indicated in FIG. 3, insulation 30 on each lead is removed so the lead makes electrical and thermal contact with the Ferrite body 28, and the Ferrite body makes thermal and electrical contact with the housing. In this manner, an electrical circuit is established between the leads and ground. As discussed in the incorporated references, the internal dc resistance, $R_{Zdc}$, of the Ferrite body is greater than the internal dc resistance, $R_L$, of the electronic device connected to the lead 18. Thus, as indicated in FIG. 3, the internal dc resistance between each lead and all other leads and between each lead and the housing is greater than the dc resistance on each lead. This prevents shorting of the dc signal on the leads. As disclosed in the incorporated documents, it has been found that a dc resistance of between 100 and 5000 ohms depending on the device's lead applications is sufficient for this purpose. However, the impedance on each lead is now a combination of the Ferrite body, the lead and the ground. This impedance is greater than the impedance existing between each lead and ground. Therefore, any potential associated with RF or electrostatic energy incident on the implant will always flow preferentially to ground rather than flowing through the leads. It has been found that an internal inductance in the range of 0.415 to 4.60 millihenries for the Ferrite body will, in combination with the above-described internal dc resistance, produce an impedance $Z_C$ that is greater than the impedance $Z_I$, yet will not interfere with any desired dc signals or other very low frequency signals that are on the leads.

Figure 4:
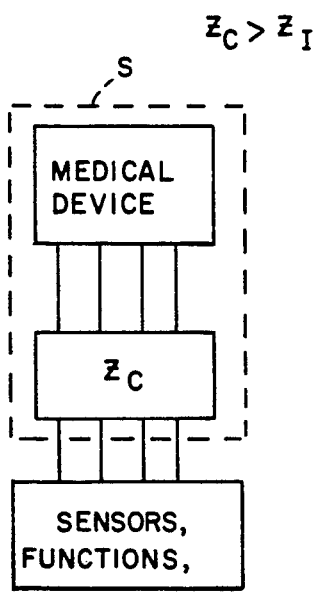
FIG. 4 is a general schematic indicating the use of the protective device in combination with any implantable electronic device.

FIG. 4 indicates a general set up for any implantable electronic device such as listed above. A complete faraday shield F is also indicated in FIG. 4.

Figure 5:
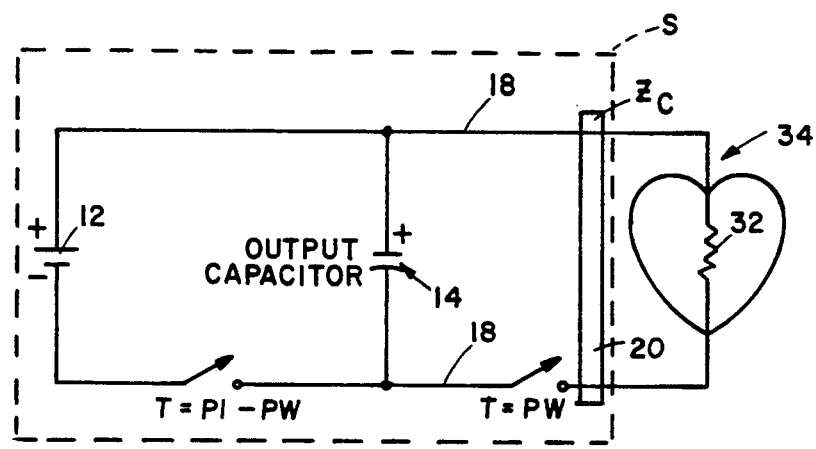
FIG. 5 is a schematic showing the protective device as applied to a simple artificial cardiac pacer.
Figure 6:
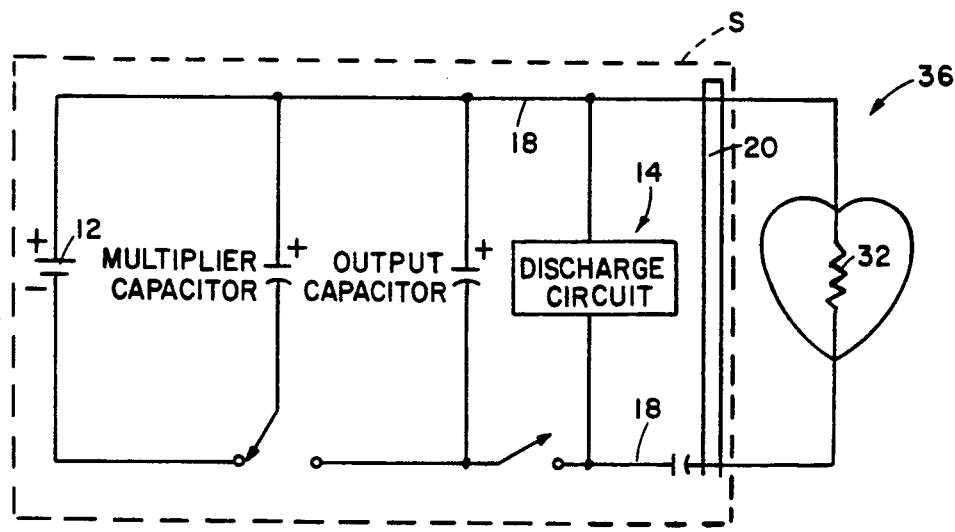
FIG. 6 is a schematic showing the protective device in combination with a more complex artificial cardiac pacer.

The application of the protective device 20 to an artificial cardiac pacer is specifically indicated in FIGS. 5-11. As indicated in FIGS. 5 and 6, the protective device is placed in thermal and electrical contact with leads 18 electrically connecting elements 32 of an artificial cardiac pacer to the power source 12 and to the controls 14. The elements 32 can be any of the elements associated with cardiac pacers such as the simple pacer 34 and the capacitive voltage-doubler pacer 36. Again a complete faraday shield F is shown in conjunction with the implantable device.

Figure 7:
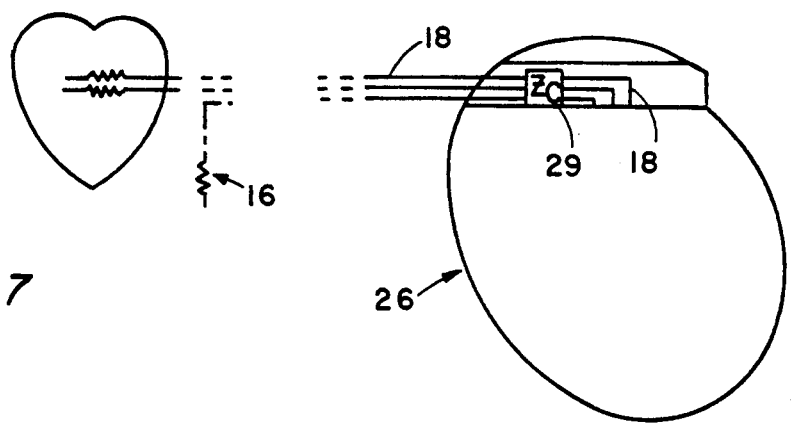
FIG. 7 is a schematic illustrating an artificial cardiac pacer having the protective device mounted inside the housing of the pacer.
Figure 8:
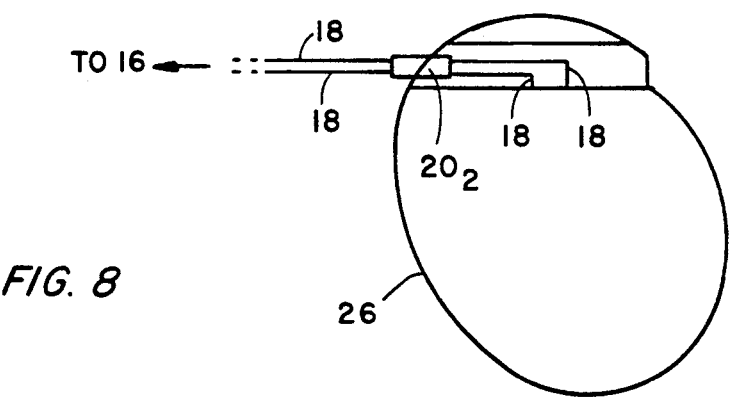
FIG. 8 is a schematic illustrating an artificial cardiac pacer having the protective device mounted to span the housing of the pacer.
Figure 9:
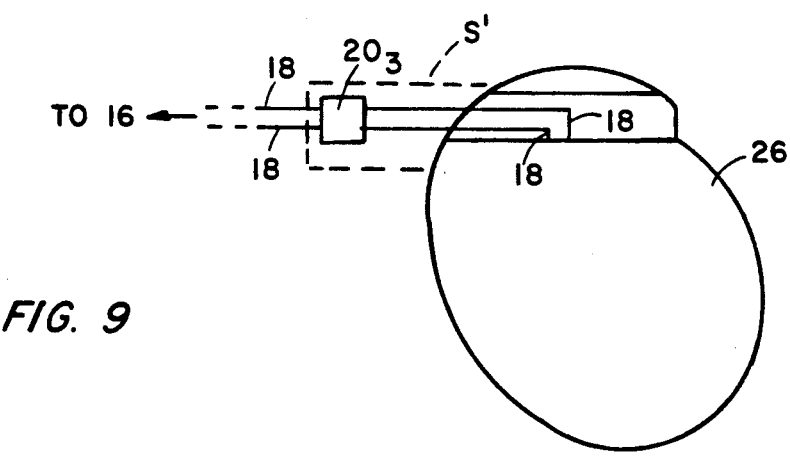
FIG. 9 is a schematic illustrating an artificial cardiac pacer having the protective device mounted outside the housing of the pacer.

As indicated in FIGS. 7, 8 and 9, the protective device 20 can be located entirely inside the housing as indicated in FIG. 7 for protective device 20', or partially inside the housing and partially outside the housing to span the housing as indicated in FIG. 8 for device $20_2$. The device can also be located entirely outside of the housing as indicated in FIG. 9 for device $20_3$. In the case of devices $20_1$ and $20_2$, the housing 26 can serve as the ground 24 and completion of the faraday shield; whereas, another RF shield and grounding cable will be used as the ground for device $20_3$. A grounding and RF shielding device S will have to be used in FIG. 9 to complete the Faraday shield and to prevent RF energy from being re-introduced downstream of protective device $20_3$. The nature of the faraday shield can be understood by comparing FIGS. 7 and 8 to FIGS. 2, 4, 5 and 6.

The patient's body can be used as the ground in some circumstances since the patient has a mass that is large enough to absorb the energy shunted thereto by the protective device without harming the patient.

In the forms of the invention shown in FIGS. 7 and 8, the housing must be a complete faraday shield. As discussed in the incorporated patent application 07/794,126 the faraday shield will effectively protect the electronic equipment inside that shield. However, an artificial cardiac pacer incorporating the protective device of the present invention will also protect the 10 elements 16 located throughout the patient's body from the deleterious effects of RF and/or electrostatic energy as well. Therefore, the entire medical prosthesis is protected by the protective device, not just the elements inside the housing.

Figure 10:
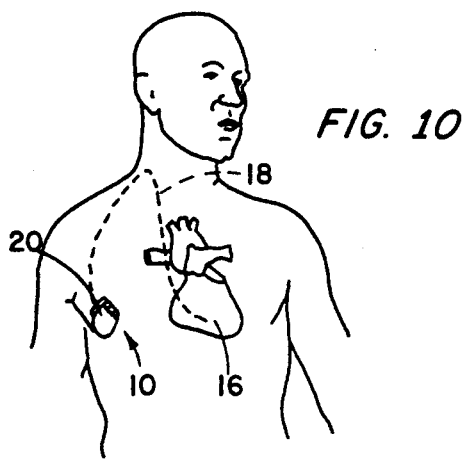
FIG. 10 illustrates the artificial cardiac pacer having the protective device thereon implanted in a user.
Figure 11:
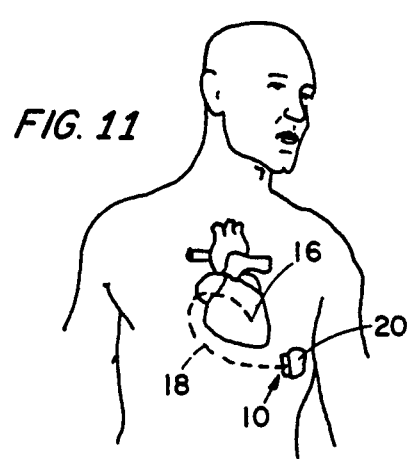
FIG. 11 illustrates the artificial cardiac pacer having the protective device thereon implanted in a user.

The use of the cardiac pacer incorporating the protective device is illustrated in FIGS. 10 and 11 for two different methods of connecting an artificial cardiac pacer to a patient's heart. The connection shown in FIG. 10 is known as an Endocardial connection, and the connection shown in FIG. 11 is known as a Myocardial and epicardial connection. As can be seen in these figures, either connection can incorporate the protective device of the present invention. In either connection, the implantable device is protected against undesired operation caused by RF and/or electrostatic energy incident thereon by inserting an impedance on the lead wires that is greater than an impedance existing between the lead wires and ground when RF energy is incident thereon.

Figure 13:
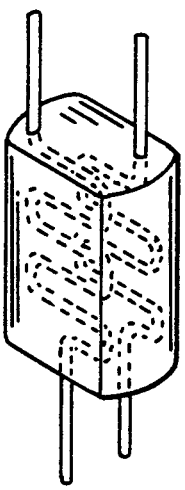
FIG. 13 illustrates a protective device having a special winding pattern for the lead.
Figure 12:
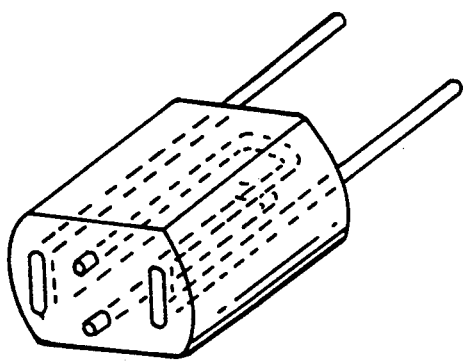
FIG. 12 illustrates a protective device having a special winding pattern for the lead.

While the protective device is shown in FIG. 3 as having a single pass through the Ferrite body for each lead, this is not intended to be limiting. The leads can be looped through the Ferrite in several patterns, as indicated in FIGS. 12 and 13, and as discussed in the incorporated patent applications. Still further, the exact chemical composition of one form of the Ferrite body is disclosed in the incorporated patent applications, and the preferred Curie Temperature is 180° C. as discussed in the incorporated documents, and the preferred 10 elemental composition for the ferrite body is $MnO_{0.45}ZnO_{0.3}FeO_{0.25}Fe_2O_4$.

While the invention has been disclosed in conjunction with active implantable prostheses, those skilled in the art will understand based, on the teaching of the present disclosure, that the invention is also applicable to passive external medical devices as well.

It is also noted that the Ferrite disclosed in the incorporated documents refers to MN-67 Ferrite and describes a controlled property ferrite that is referred to as MN-68.

It is understood that while certain forms of the present invention have been illustrated and described herein, it is not to be limited to the specific forms or arrangements of parts described and shown.

We claim:

1. An electronic prosthesis that is implantable into a user's body including:
   A) an electronic device that is implantable into a user's body and includes a dc power source, electronic control elements, tissue stimulating elements and an electronic lead wire electrically connecting said power source, said electronic control elements and said tissue stimulating elements; and
   B) a protective device for protecting said electronic device from undesired RF energy induced operation and from undesired electrostatic energy induced operation, said protective device including
      (1) a ground element having a first impedance and electrically separated from said lead wire be said first impedance, and
      (2) an impedance element in said lead wire connected between said dc power source and said tissue stimulating elements having an impedance that is greater than said first impedance when exposed to RF energy.

2. The electronic prosthesis defined in claim 1 wherein said ground element includes a conductive housing for said electronic device.

3. The electronic prosthesis defined in claim 2 wherein said impedance element is-thermally connected to said lead wire and to said conductive housing.

4. The electronic prosthesis defined in claim 1 wherein said impedance element is electrically connected to said ground element.

5. The electronic prosthesis defined in claim 1 wherein said impedance element includes a Ferrite body.

6. The electronic prosthesis defined in claim 5 wherein said Ferrite body has a Curie Temperature greater than 180° C.

7. The electronic prosthesis defined in claim 5 wherein said Ferrite element includes MN-67 Ferrite.

8. The electronic prosthesis defined in claim 7 wherein said Ferrite element has an elemental formulation of. $MnO_{0.45}ZnO_{0.3}FeO_{0.25}Fe_2O_4$.

9. The electronic prosthesis defined in claim 1 wherein said electronic device is an artificial cardiac pacer.

10. The electronic prosthesis defined in claim 8 wherein said artificial cardiac pacer includes a conductive housing and said impedance element is located inside said conductive housing and is grounded to said housing.

11. The electronic prosthesis defined in claim 9 wherein said cardiac pacer includes a conductive housing and said impedance element is partially located inside said conductive housing and partially located outside said housing to span said conductive housing.

12. The electronic prosthesis defined in claim 9 wherein said cardiac pacer includes a housing and said impedance element is located outside said housing with RF shielding and grounding cables forming form a complete Faraday shield.

13. The electronic prosthesis defined in claim 9 wherein said artificial cardiac pacer includes a conductive housing and said impedance element is located with respect to said conductive housing so that said housing forms a complete Faraday shield.

14. The electronic prosthesis defined in claim 1 wherein said lead wire is wound through said impedance element in an arcuate pattern.

15. An electronic prosthesis that is implanted into a user's body including:
   A) an electronic device that is implanted into a user's body and includes a metal housing having an opening, a dc power source inside said metal housing, electronic control elements inside said metal housing, tissue stimulating elements and an electronic lead wire electrically connecting said power source and extending through said opening, said electronic control elements and said tissue stimulating elements; and
   B) a protective device for protecting said electronic device from undesired RF energy induced operation and from undesired electrostatic energy induced operation, said protective device including
      a closure element covering said case open end and including a ground element having a first impedance and electrically connected to said lead wire, and
      said lead wire having an impedance between said power source and said tissue stimulating elements which is greater than said first impedance when exposed to RF energy.

16. An electronic prosthesis that is implanted into a user's body including:
   A) an electronic device that is implanted into a user's body and includes a dc power source, electronic control elements, a tissue stimulating element and an electronic lead wire electrically connecting said power source, said electronic control elements and said tissue stimulating element, said tissue stimulating element having a dc resistance; and B) a protective device for protecting said electronic device from undesired RF energy induced operation and from undesired electrostatic energy induced operation, said protective device including
  (1) a ground element having a first impedance and electrically separated from said lead wire by and first impedance, and
  (2) an impedance element in said lead wire connected between said dc power source and said tissue stimulating element and having an impedance that is greater than said first impedance when exposed to RF energy, said impedance element having a dc resistance that is greater than the dc resistance said tissue stimulating element.

17. A method for preventing undesired operation of an implantable medical prosthesis comprising: preventing RF and electrostatic energies from reaching the circuitry of an electronic medical prosthesis by placing impedance elements in the lead wires associated with the medical prosthesis so that the impedance of the lead wires exceeds the impedance between such lead wires and ground when exposed to RF energy.

18. The method defined in claim 17 further including a step of using a Ferrite device as the impedance.

19. The method defined in claim 18 further including a step of maintaining the inductance of the Ferrite to be in a range of 0.415 to 4.60 millihenries and to have a dc resistance in a range of between 100 and 5000 ohms.

20. An electronic prosthesis that is implantable into a user's body including:
A) an electronic device that is implantable into a user's body and includes a dc power source, electronic control elements, tissue stimulating elements and an electronic lead wire electrically connecting said power source, said electronic control elements and said tissue stimulating elements; and
B) a protective device for protecting said electronic device from undesired RF energy induced operation and from undesired electrostatic energy induced operation, said protective device including
  (1) a ground element electrically separated from said lead wire by said first impedance, and
  (2) an impedance element in said lead wire connected between said electronic control elements and said tissue stimulating elements and having an impedance that is greater than said first impedance when exposed to RF energy.

21. The electronic prosthesis defined in claim 5 wherein said Ferrite element includes MN-68 Ferrite.

* * * * *